United States Patent [19]

Krishnan

[11] Patent Number: 4,632,949
[45] Date of Patent: Dec. 30, 1986

[54] FLAME RETARDING AGENTS FOR POLYCARBONATES

[75] Inventor: Sivaram Krishnan, Pittsburgh, Pa.

[73] Assignee: Mobay Chemical Corporation, Pittsburgh, Pa.

[21] Appl. No.: 687,783

[22] Filed: Dec. 31, 1984

[51] Int. Cl.$^4$ .................. C08K 5/34; C07D 209/48
[52] U.S. Cl. ...................... 524/94; 524/165; 524/409; 524/539; 524/540; 524/546; 548/401; 548/462; 548/476
[58] Field of Search .............. 524/94, 165, 409, 539, 524/540, 546; 548/401, 462, 476

[56] References Cited

U.S. PATENT DOCUMENTS

| | | | |
|---|---|---|---|
| 3,775,367 | 11/1973 | Nouvertne | 260/45.9 R |
| 3,868,388 | 2/1975 | Dotson, Jr. et al. | 260/326 N |
| 3,873,567 | 3/1975 | Cyba | 260/326 C |
| 3,915,930 | 10/1975 | Dotson, Jr. et al. | 260/45.8 |
| 3,919,167 | 11/1975 | Mark | 260/45.8 N |
| 3,923,734 | 12/1975 | Dotson, Jr. et al. | 260/45.75 B |
| 3,933,734 | 1/1976 | Mark et al. | 260/45.7 S |
| 3,940,366 | 2/1976 | Mark | 260/45.9 R |
| 3,971,756 | 7/1976 | Bialous et al. | 260/45.7 R |
| 3,987,056 | 10/1976 | Cobb | 548/476 |
| 4,001,179 | 1/1977 | Richter et al. | 260/45.75 B |
| 4,003,862 | 1/1977 | Albright | 260/2.5 AJ |
| 4,066,618 | 1/1978 | Mark | 260/45.85 T |
| 4,067,846 | 1/1978 | Mark | 260/45.9 K |
| 4,069,201 | 1/1978 | Mark | 260/45.95 R |
| 4,073,678 | 2/1978 | Hammond et al. | 162/19 |
| 4,075,164 | 2/1978 | Mark | 260/45.7 S |
| 4,087,441 | 5/1978 | Lee | 260/326 N |
| 4,093,589 | 6/1978 | Factor et al. | 260/45.75 |
| 4,208,489 | 6/1980 | Schmidt et al. | 524/94 |
| 4,223,100 | 9/1980 | Reinert | 524/411 |
| 4,320,049 | 3/1982 | Krishnan et al. | 524/94 |

FOREIGN PATENT DOCUMENTS 1287934 9/1972 United Kingdom .

Primary Examiner—John Kight
Assistant Examiner—K. Morgan
Attorney, Agent, or Firm—Gene Harsh; Joseph C. Gil; Aron Preis

[57] ABSTRACT

The present invention relates to novel N-(alkoxyphenyl) phthalimides conforming to the structure

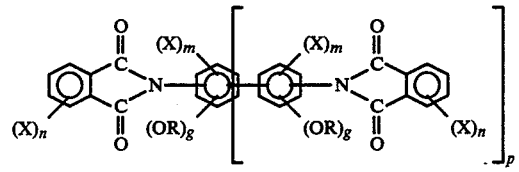

wherein X is a halogen atom, R is a $C_1$–$C_4$ alkyl, g is 1 to 5, n is an integer of from 0 to 4, m is either 0 or 1 and p is either 0 or 1. The phthalimide thus disclosed was found to be suitable as a flame retarding additive for thermoplastic molding compositions, especially compositions comprising polycarbonate resins.

14 Claims, No Drawings

FLAME RETARDING AGENTS FOR POLYCARBONATES

FIELD OF THE INVENTION

The invention relates to flame retarding compounds suitable for improving the flame resistance of thermoplastic compositions and more particularly to N-(alkoxyphenyl)phthalimides.

SUMMARY OF THE INVENTION

The presently disclosed novel N-(alkoxyphenyl)phthalimides conform to

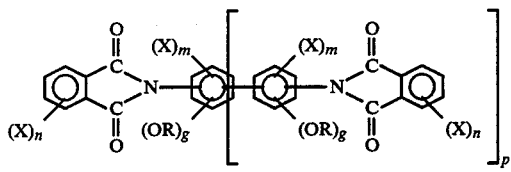

wherein X is a halogen, preferably chlorine or bromine, R is a $C_1$–$C_4$ alkyl, preferably methyl, g is an integer between 1 and 5, preferably 1 or 2, n is an integer from 0 to 4, preferably 1 to 2, m is either 0 or 1, preferably 0 and p is either 0 or 1, preferably 0, is an effective flame retarding agent suitable in improving the flammability rating of thermoplastic molding compositions. Particularly, the molding compositions thus improved comprise a polycarbonate resin.

BACKGROUND OF THE INVENTION

Flame retarding additives for use in polymeric compositions include phosphates, phosphoric acid esters and thio-phosphoric acid esters containing halogenated alkyl radicals. Also, metal salts notably sulfonate salts of alkali or alkaline earth metals have been disclosed to improve the flame retardance of polycarbonates. Further, chlorine or bromine substitutions in some of the phenolic diols used in the preparation of polycarbonates have been disclosed to impart flame retardance to the polycarbonate resin.

Illustrative of the sulfonic acid salts and of metal salts are those disclosed in U.S. Pat. Nos. 3,775,367; 4,067,846; 4,073,678; 4,075,164; 4,066,618; 4,069,201; 4,093,589; 3,971,756; 3,933,734; 3,940,366 and 3,919,167.

Some of these flame retardants, however, in order to be effective, are added in relatively large amounts such as to adversely effect some of the desirable properties of the base resin. For example, both the impact strength and the hydrolytic stability are compromised upon addition of large quantities of salt. Further, many of these flame retarding salts are susceptible to volatilization at the high molding temperatures of polycarbonates, necessitating thus the addition of excess amounts of salt which in turn bring about haze and loss of transparency. Since there is no uniformity of processing conditions among molders, it becomes difficult, if not impossible, to regulate the ultimate amount of salt incorporated into the resins.

Flame retardants incorporating a phthalimide group have been disclosed in, for instance, British Pat. No. 1,287,934 and U.S. Pat. Nos. 3,873,567; 3,923,734; 3,915,930; 3,868,388; 4,087,441; 4,001,179; 4,003,862 and 4,320,049.

DETAILED DESCRIPTION OF THE INVENTION

The preparation of the novel compounds of the invention may be carried out by condensing, in a suitable solvent, the corresponding phthalic anhydride and an appropriate alkoxyaniline. Generally, the phthalic anhydride corresponds to

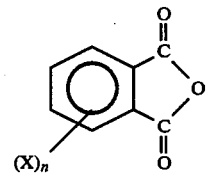

wherein X is a halogen, preferably chlorine or bromine and n is 0 to 4, preferably 1 to 2.

The suitable alkoxyaniline may carry 1 to 5, preferably 1 or 2, alkoxy substituents which are any of $C_1$–$C_4$ alkoxy groups.

The suitable solvent in the context of preparing the novel compounds of the invention are any one of acetic acid and aprotic solvents such as dimethyl formamide, dimethyl acetamide, N-methyl pyrrolidone and n-methyl caprolactam. Also suitable are hydrocarbon solvents such as toluene, xylene and o-dichlorobenzene.

The flame retarding agent of the invention is useful in improving the flame resistance of thermoplastic molding compositions comprising polycarbonate resin and the articles formed therefrom.

Due in part to their low volatility and to their relatively low melt temperature the compounds of the invention prove to be particularly suitable in the preparation of polycarbonate based molding compositions. The compounds are substantially soluble in polycarbonate resins at the processing temperature of the resin and produce clear compositions, and moldings prepared therefrom, which have good light transmission and virtual freedom from haze.

The polycarbonate resins useful in the practice of the invention are homopolycarbonate, copolycarbonate and terpolycarbonate resins or mixtures thereof. The polycarbonate resins generally have molecular weights of 10,000–200,000 (weight average molecular weight) preferably 20,000–80,000, and may alternatively be characterized by their melt flow of 1–24 gm/10 min. at 300° C. per ASTM D-1238. These polycarbonates may be prepared, for example, by the known two phase interface process from phosgene and dihydroxy compounds by polycondensation (see German OS Nos. 2,063,050; 2,053,052; 1,570,703; 2,211,956; 2,211,957 and 2,248,817 and French Pat. No. 1,561,518 and the monograph, H. Schnell, *Chemistry and Physics of Polycarbonates*, Interscience Publishers, New York, 1964, all incorporated herein by reference).

In the present context, dihydroxy compounds suitable for the preparation of the polycarbonates of the invention conform to the structural formulae (1) or (2)

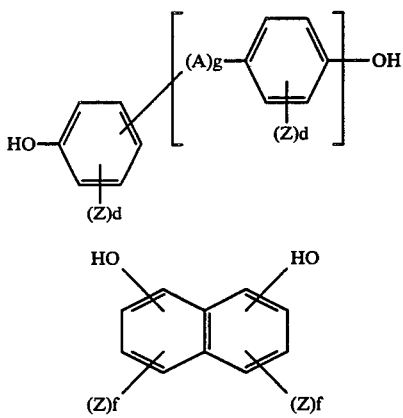

wherein

A denotes an alkylene group with 1 to 8 carbon atoms, an alkylidene group with 2 to 8 carbon atoms, a cycloalkylene group with 5 to 15 carbon atoms, a cycloalkylidene group with 5 to 15 carbon atoms, a carbonyl group, an oxygen atom, a sulfur atom, an —SO— or —SO$_2$— radical; a radical of the general formula

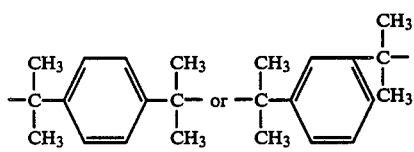

g denotes the number 0 or 1;

e denotes the number 0 or 1;

Z denotes F, Cl, Br or a C$_1$–C$_2$ alkyl and if several Z radicals are substituents in one aryl radical, they may be identical or different;

d denotes 0 or an integer of from 1 to 4; and f denotes 0 or an integer of from 1 to 3.

Among the useful dihydroxy compounds in the practice of the invention are hydroquinone, resorcinol, bis-(hydroxyphenyl)-alkanes, bis-(hydroxyphenyl)-cycloalkanes, bis-(hydroxyphenyl)-ethers, bis-(hydroxyphenyl)-ketones, bis-(hydroxyphenyl)-sulfides, bis-(hydroxyphenyl)-sulfoxides, bis-(hydroxyphenyl)-sulfones and α,α-bis(hydroxyphenyl)-diisopropyl-benzenes. These and further suitable aromatic dihydroxy compounds are described, for example, in U.S. Pat. Nos. 3,028,365; 2,999,835; 3,148,172; 3,271,368; 2,991,273; 3,271,367; 3,280,078; 3,014,891 and 2,999,846 (all incorporated herein by reference), in German Offenlegungsschriften (German Published Specifications) Nos. 1,570,703; 2,063,050; 2,063,052; 2,211,956 and 2,211,957, in French Patent Specification No. 1,561,418 and in the monograph, H. Schnell, *Chemistry and Physics of Polycarbonates*, Interscience Publishers, New York, 1964. Further examples of suitable dihydroxy compounds are 2,2-bis-(4-hydroxyphenyl)-propane (bisphenol A), 2,4-bis-(4-hydroxyphenyl)-2-methyl-butane, 1,1-bis-(4-hydroxyphenyl)-cyclohexane, α,α-bis-(4-hydroxyphenyl)-p-diisopropyl-benzene, 2,2-bis-(3-chloro-4-hydroxyphenyl)-propane, hydroxybenzophenone and 4,4'-sulfonyl diphenol; the most preferred one is 2,2-bis-(4-hydroxyphenyl)-propane (bisphenol A).

The polycarbonates of the invention may entail in their structure, units derived from one or more of the suitable bisphenols.

The preparation of polycarbonate resins may be carried out in accordance with any of the processes known in the art, for example, by the interfacial polycondensation process, polycondensation in a homogeneous phase or by transesterification.

The suitable processes and the associated reactants, catalysts, solvents and conditions are known in the art and have been described, inter alia, in German Pat. Nos. 1,046,311 and 962,274 and in U.S. Pat. Nos. 3,248,414; 3,153,008; 3,215,668; 3,187,065; 3,028,365; 2,999,846; 2,999,835; 2,964,974; 2,970,137; 3,912,638 and 1,991,273.

In the preparation of the polycarbonate resins of the invention monofunctional reactants such as monophenols may be used in order to limit their respective molecular weights. Also, branching agents may be employed. Branching may be obtained by the incorporation of small amounts, preferably of between about 0.05 and 2.0 mol % (relative to diphenols employed), of trifunctional or more than trifunctional compounds, especially compounds having three or more phenolic hydroxyl groups. Polycarbonates of this type are described, for example, in German Offenlegungsschriften (German Published Specifications) Nos. 1,570,533; 1,595,762; 2,116,974 and 2,113,347; British Specification No. 1,079,821 and U.S. Pat. No. 3,544,514 (incorporated herein by reference).

Some examples of compounds with three or more than three phenolic hydroxyl groups which can be used are phloroglucinol, 4,6-dimethyl-2,4,6-tri-(4-hydroxyphenyl)-heptane, 2,4,6-trimethyl-2,4,6-tri-(4-hydroxyphenyl)-heptane, 1,4,5-tri-(4-hydroxyphenyl)-benzene, 1,1,1-tri-(4-hydroxyphenyl)-ethane, tri-(4-hydroxyphenyl)-phenylmethane, 2,2-bis[4,4-bis-(4-hydroxyphenyl)-cyclohexyl]-propane, 2,4-bis-(4-hydroxyphenylisopropyl)-phenol, 2,6-bis-(2-hydroxy-5'-methylbenzyl)-4-methylphenol, 2-(4-hydroxyphenyl)-2-(2,4-dihydroxyphenyl)-propane, hexa(4-(4-hydroxyphenylisopropyl)phenyl)-ortho-terephthalic acid ester, tetra-(4-hydroxyphenyl)-methane, tetra-(4-(4-hydroxyphenylisopropyl)-phenoxy)-methane and 1,4-bis-((4',4"-dihydroxy-tri phenyl)-methyl)-benzene. Some of the other trifunctional compounds are 2,4-dihydroxy-benzoic acid, trimesic acid, cyanuric chloride and 3,3-bis-(4-hydroxyphenyl)-2-oxo-2,3-dihydroindole.

Among the resins suitable in the practice of the invention are included phenolphthalein-based polycarbonate, copolycarbonates and terpolycarbonates such as are described in U.S. Pat. Nos. 3,036,036 and 4,210,741, both incorporated by reference herein.

The flame retarding agent of the invention is incorporated in the thermoplastic polycarbonate resins in an amount sufficient to bring about an improvement in the flame retardance of these resins, preferably the amount thus incorporated is between about 0.01 and about 1.0 percent, more preferably between about 0.1 and about 0.75 percent, said percent being relative to the total weight of said resin and said flame retarding agent.

In preferred embodiments of the invention, the compositions further contain small amounts of sulfonic or carboxylic acid salt. Specifically, the sulfonic or carboxylic acid salt is present in an amount of about 0.01 to about 3 percent, most preferably 0.05 to about 1 percent relative to the weight of the thermoplastic resin. Suitable sulfonic acid salts have been disclosed in U.S. Pat. No. 3,775,367 and in U.S. Pat. No. 4,391,935, both incorporated herein by reference.

The preferred sulfonic acid salts are sodium or potassium perfluorobutane sulfonates.

Examples of suitable carboxylic acid salts in the sense of the invention are the alkali metal salts, especially the sodium salts and potassium salts, of aliphatic, aromatic or aliphatic-aromatic monobasic or dibasic, optionally halogenated, carboxylic acids with 1 to 24 carbon atoms, including those of formic acid, acetic acid, propionic acid, butyric acid, isobutyric acid, valeric acid, caproic acid, oenanthic acid, caprylic acid, pelargnoic acid, capric acid, lauric acid, stearic acid, 3-(3,5-di-tert.-butyl-4-hydroxyphenyl)-propionic acid, oleic acid, oxalic acid, malonic acid, succinic acid, glutaric acid, adipic acid, pimelic acid, sebacic acid, benzoic acid and its p-alkylated derivatives with 1 to 8 carbon atoms in the alkyl radical, salicylic acid, terephthalic acid, isophthalic acid, phthalic acid monobenzyl ester, diglycolic acid monodecyl ester, adipic acid monobutyl ester and 3-chlorobenzoic acid.

An additional preferred embodiment entails admixing with the compositions of the invention an alkali metal salt of an inorganic acid. Lithium, sodium and potassium salts are preferred. Suitable inorganic acids include any compound which does not contain a carbon atom and meets the traditional tests of acidity. Among the suitable acids are the mineral acids and other Lewis acids which do not contain carbon atoms. Preferred acids are those that form salts with alkali metals which gave pH values of about 7 or less when dissolved in water.

The most preferred alkali salts of an inorganic acid are the inorganic alkali metal complex fluoro anion salts, this terminology being derived from the discussion of fluorine compounds contained in the text Advanced Inorganic Chemistry by F. A. Cotton and G. Wilkinson, Interscience Publishers, 1962, at pages 290–294, these pages being incorporated herein by reference. Suitable inorganic alkali metal complex fluoro anion salts include $KBF_4$, $K_3AlF_6$, $KAlF_4$, $K_2SiF_6$, $Na_3AlF_6$, $KPF_6$, $NaSbF_6$, $Na_3FeF_6$, $NaPF_6$, $Na_2SiF_6$, $Na_2TiF_6$, $NaBF_4$, $K_2TaF_7$, $K_2NbF_7$, $KSbF_6$, $K_2NiF_6$, $K_2TiF_6$, $LiBF_4$, $LiPF_6$ and $LiBeF_4$.

$KBF_4$, $K_3AlF_6$, $KAlF_4$, $K_2SiF_6$ and $Na_3AlF_6$ are the preferred inorganic alkali metal complex fluoro anion salts, and $Na_3AlF_6$ is the most preferred inorganic alkali metal complex fluoro anion salt.

The inorganic alkali metal complex fluoro anion salts may be used in an effective amount up to about 2 wt. % based on the weight of the polymer resin. It is preferred to use no less than about 0.01 wt. % and more preferably no less than about 0.1 wt. %. It is also preferred to use no more than about 1 wt. % and more preferably about 0.5 wt. %. Amounts higher than 2 wt. % of salt will not decrease its effect upon flame retardance but may cause a degree of degradation in the other properties of the resin greater than is justified by the improvement in flame retardancy.

Naturally, any particular salt which is known to have characteristics likely to make it unacceptable for use in polymer resins should be avoided. For instance, salts which decompose at the processing temperatures of the resins into which they are incorporated should be avoided.

The thermoplastic molding compositions of the invention may contain further flame retarding additives and drip suppressants, for instance PTFE (i.e., polytetrafluoroethylene) an ASTM type 3 (fibrillating type). Other additives such as are commonly used in thermoplastic molding compositions, including reinforcing agents, fillers, pigments, dyes, UV stabilizers, hydrolytic stabilizers, mold release agents and plasticizers may be incorporated as well.

The invention is further illustrated, but is not intended to be limited by the following examples in which all parts and percentages are by weight unless otherwise specified.

EXAMPLES

Compositions in accordance with the present invention were prepared and their properties determined. The table below summarizes the properties of these molding compositions all of which were based on a homopolycarbonate of bisphenol-A which is characterized in that its melt flow rate (per ASTM D-1238) is about 6–11.9 gm/10 min. (Merlon M-40 from Mobay Chemical Corporation). Each of the compositions contained 0.5%, relative to its weight, of an imide in accordance with the invention. The particular imide used in each of the compositions is identified in the table in terms of its molecular structure. In addition to the indicated imide, the compositions each contained about 0.4% of polytetrafluoroethylene (ASTM type 3) and 0.3% of cryolite. Also, each composition contained 0.3% of a mold release agent (pentaerythritol tetrastearate) and a pigment, neither of which are believed critical in the present context.

The compositions were first extruded (1½" Waldron Hartig, 2.75:1 screw with mixing pins, at 60 rpm; 20, 40, 60, 20 screen pack at a temperature profile (°F.): rear zone 500–520, middle 500–515, front 510–520, die 510; melt temperature 495°–505° F. Test specimens were injection molded under the following processing parameters: primary injection pressure 900 psi, secondary injection pressure 700 psi, 35 second cycles; temperature profile (°C.): front 550° C., nozzle 520° C., middle 550° C.

| Added imide | Melt flow (gm/10 min) | Impact strength (1) ⅛" (ft-lb/in) | ¼" (ft-lb/in) | UL-94, 1/16" | UL-94, 5V |
|---|---|---|---|---|---|
| 1 | 11.3 | 2.1 | 1.5 | V-0 (0.8) | passed |
| 2 | 10.9 | 2.0 | 1.4 | V-0 (0.1) | passed |
| 3 | 11.2 | 2.3 | 1.5 | V-0 (0.9) | passed |
| 4 | 10.7 | 2.6 | 1.6 | V-0 (0) | passed |
| 5 | 11.9 | 2.1 | 1.5 | V-0 (0.2) | passed |
| 6 | 11.1 | 2.9 | 1.6 | V-0 (0) | passed |
| 7 | 11.7 | 2.3 | 1.7 | V-0 (1.5) | passed |
| 8 | 12.0 | 2.4 | 1.7 | V-0 (0.4) | passed |

(1) Izod, Notched
(2) The numbers in parenthesis denote average burn time in seconds.
*The imides added are described below.

1. 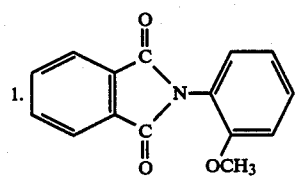

melting point (m.p.) 148–149° C.

| Added imide | Melt flow (gm/10 min) | Impact strength (1) (ft-lb/in) ⅛" | ¼" | UL-94, 1/16" | UL-94, 5V |
|---|---|---|---|---|---|

2. 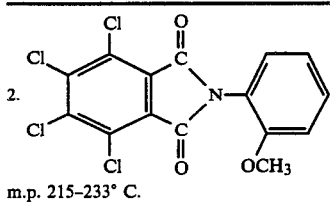
m.p. 215-233° C.

3. 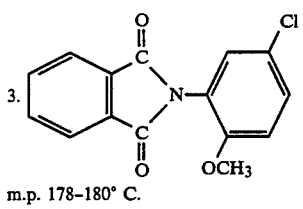
m.p. 178-180° C.

4. 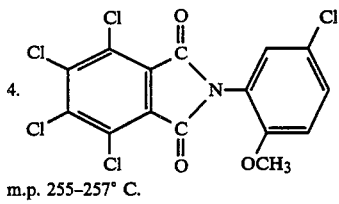
m.p. 255-257° C.

5. 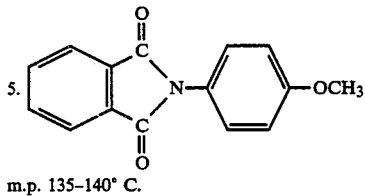
m.p. 135-140° C.

6. 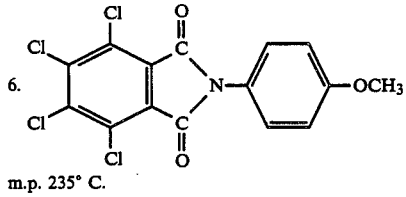
m.p. 235° C.

7. 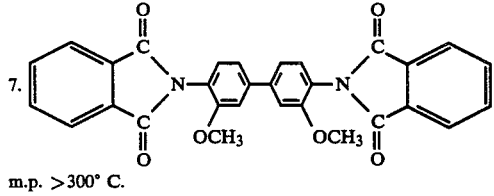
m.p. >300° C.

8. 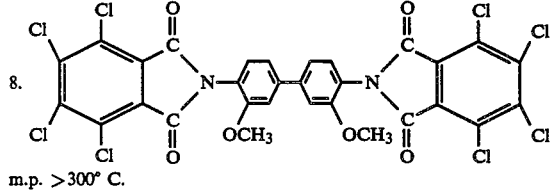
m.p. >300° C.

It is important to note that prior art compounds similar to the novel compounds of the present invention except for the absence therefrom of the claimed methoxy substituent, failed the UL-94 5 V test. Also, formulations which contained no imide moiety failed that test.

The invention has been described with particular reference to specific materials yet such should not be viewed as in any way limiting the scope of the invention which is set forth in the following claims.

What is claimed is:

1. The compound

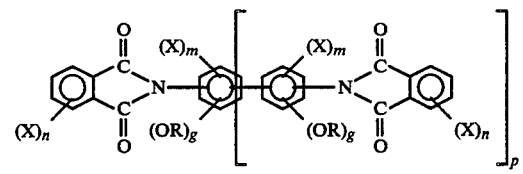

wherein X is a halogen atom, R is a $C_1$–$C_4$ alkyl, g is 1 to 5, n is an integer from 0 to 4, m is either 0 or 1 and p is 1.

2. The compound

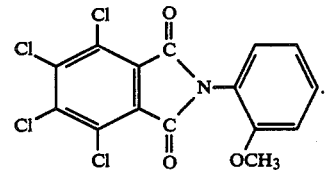

3. The compound

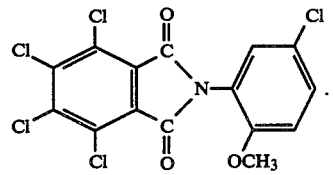

4. The compound

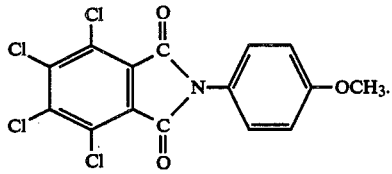

5. The compound

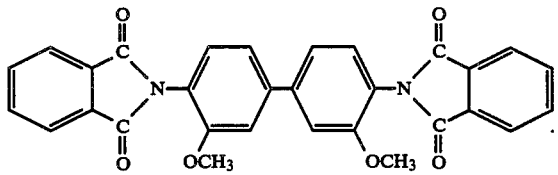

6. The compound

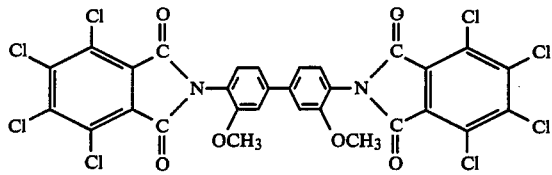

7. A thermoplastic molding composition comprising (i) a thermoplastic aromatic polycarbonate resin and (ii) a flame retarding amount of a compound conforming to

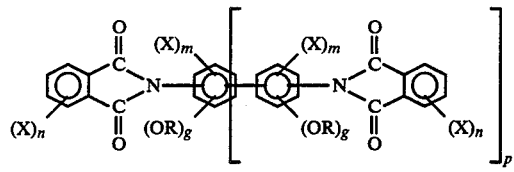

wherein X is a halogen atom, R is a $C_1-C_4$ alkyl, g is 1 to 5, n is an integer of from 0 to 4, m is either 0 or 1 and p is either 0 or 1.

8. The composition of claim 7 wherein said resin is a homopolycarbonate based on bisphenol-A.

9. The composition of claim 8 wherein said resin is branched.

10. The composition of claim 7 wherein said amount is between 0.01 and about 1.0 percent relative to the weight of said resin.

11. The composition of claim 7 further comprising about 0.01 to about 2 percent relative to the weight of the resin of an alkali salt of an inorganic acid.

12. The composition of claim 11 further comprising sufficient amounts of PTFE to render the composition V-0 for 1/16″ specimens in accordance with UL-94.

13. The composition of claim 12 wherein said alkali salt of an inorganic acid is cryolite.

14. A thermoplastic molding composition comprising (i) a thermoplastic aromatic polycarbonate resin and (ii) a flame retarding amount of a compound conforming to

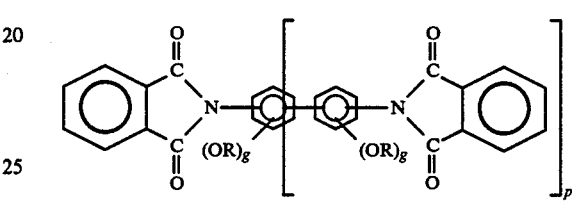

wherein R is $C_1-C_4$ alkyl, g is 1-5 and p is 0 or 1.

* * * * *